US009546958B2

United States Patent
Shih (10) Patent No.: US 9,546,958 B2
(45) Date of Patent: Jan. 17, 2017

(54) METHOD OF STAMPING SURFACE-ENHANCE RAMAN SPECTROSCOPY FOR LABEL-FREE, MULTIPLEXED, MOLECULAR SENSING AND IMAGING

(71) Applicant: UNIVERSITY OF HOUSTON SYSTEM, Houston, TX (US)

(72) Inventor: Wei-Chuan Shih, Houston, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 72 days.

(21) Appl. No.: 14/699,025

(22) Filed: Apr. 29, 2015

(65) Prior Publication Data

US 2015/0308960 A1 Oct. 29, 2015

Related U.S. Application Data

(60) Provisional application No. 61/985,984, filed on Apr. 29, 2014.

(51) Int. Cl.
*G01J 3/44* (2006.01)
*G01N 21/65* (2006.01)
*B82Y 30/00* (2011.01)
*G01J 3/02* (2006.01)

(52) U.S. Cl.
CPC .............. *G01N 21/658* (2013.01); *B82Y 30/00* (2013.01); *G01J 3/02* (2013.01); *G01J 3/44* (2013.01)

(58) Field of Classification Search
CPC .... G01N 21/65; G01N 21/656; G01N 21/658; G01J 3/02; G01J 3/44
See application file for complete search history.

(56) References Cited

U.S. PATENT DOCUMENTS

| 2004/0009298 A1* | 1/2004 | Moran ................... H05K 3/182 427/304 |
| 2012/0081703 A1 | 4/2012 | Moskovits et al. |
| 2012/0309080 A1 | 12/2012 | Cunningham et al. |
| 2014/0002816 A1 | 1/2014 | Liu et al. |
| 2014/0104606 A1 | 4/2014 | Shih |

FOREIGN PATENT DOCUMENTS

WO 2006/134376 A2 12/2006

OTHER PUBLICATIONS

Lee, Chang H., et al.; Paper Based SERS Swab for Rapid Trace Detection on Real-World Surfaces; Applied Materials & Interfaces, vol. 2, No. 12, 3429-3435, 2010.

(Continued)

*Primary Examiner* — Abdullahi Nur
(74) *Attorney, Agent, or Firm* — Jackson Walker LLP (57) ABSTRACT

The present disclosure relates the use of a stamping surface enhanced Raman scattering (S-SERS) technique with nanoporous gold disk (NPGD) plasmonic substrates to produce a label-free, multiplexed molecular sensing and imaging technique. A NPGD SERS substrate is stamped onto a surface containing one or more target molecules, followed by SERS measurement of the target molecules located between the surface and SERS substrate. The target molecules may be deposited on the surface, which may be a carrier substrate such as polydimethylsiloxane (PDMS).

21 Claims, 11 Drawing Sheets (56) References Cited

OTHER PUBLICATIONS

Li, Jian Feng, et al.; Shell-Isolated Nanoparticle-Enhanced Raman Spectroscopy; Nature, vol. 464, 392-395, 2010.
Qi, Ji, et al.; Surface-Enhanced Raman Spectroscopy With Monolithic Nanoporous Gold Disk Substrates; Nanoscale, vol. 5, 4105-4109, 2013.
Wang, Hui, et al; Quantitative Analysis of Creatinine in Urine by Metalized Nanostructured Parylene, vol. 15, No. 2, 027004-1-5, 2010.
Korean Intellectual Property Office; International Search Report and Written Opinion; PCT Application No. PCT/US2015/028135; Jul. 29, 2015.

\* cited by examiner

METHOD OF STAMPING SURFACE-ENHANCE RAMAN SPECTROSCOPY FOR LABEL-FREE, MULTIPLEXED, MOLECULAR SENSING AND IMAGING

This application claims priority to U.S. Provisional Patent Application Ser. No. 61/985,984, entitled "Method of Stamping Surface-Enhance Raman Spectroscopy for Label-Free, Multiplexed, Molecular Sensing and Imaging," filed on Apr. 29, 2014, the entire contents of which are hereby incorporated by reference.

This invention was made with government support under Grant No. 50560 awarded by the National Science Foundation, Grant No. G105289 awarded by NASA, Grant No. G105128 awarded by GoMRI, National Science Foundation (NSF) CAREER Award CBET-1151154, National Aeronautics and Space Administration (NASA) Early Career Faculty Grant NNX12AQ44G, and a grant from Gulf of Mexico Research Initiative GoMRI-030. The United States Government has certain rights in the invention.

BACKGROUND

Surface-enhanced Raman spectroscopy (SERS) is a spectroscopic technique, where Raman scattering is boosted primarily by enhanced electric field due to localized surface plasmon resonance (LSPR). With advances in nanofabrication techniques, SERS has attracted great attention for label-free molecular sensing and imaging. However, the practical use of SERS has often encountered a couple of inherent issues. The first one is regarding a molecule transfer step where target molecules need to be within the close proximity of a SERS-active surface by either mixing with nanoparticles or coating onto surface-bound nanostructures. In other words, target molecules are required to be transferred from non-SERS-active surfaces to SERS-active ones, normally in the solution phase, which can be problematic due to issues such as surface affinity variability and uncertainty, competitive adsorption among different molecules, and contamination issues, causing irreproducible results and erroneous or biased interpretations. More importantly, if the spatial distribution of molecules on the surface prior to the transfer step is of importance, such information is completely lost. Practically, solution-phase processes are relatively more labor and time-consuming and require a "wet" laboratory. Furthermore, SERS measurements are always restricted to molecules adsorbed on metals such as Ag, Au, and Cu.

To address the aforementioned issues, many approaches have been developed, and can be broadly classified into chemical and physical means. Chemical approaches employ functionalized surfaces to improve affinity and selectivity of target molecules. For example, Au nanoparticles were surface-modified by cystamine and cysteine for detecting perchlorate and trinitrotoluene, respectively. Physical approaches, in contrast, attempt to bring the target molecules to the SERS-active surface by physical manipulation. A potential advantage of physical approach lies in that the SERS enhancement depends solely on distance, rather than surface affinity. For example, tip-enhanced Raman scattering (TERS) technique introduces enhanced electromagnetic field by bringing a nano-tip into the vicinity of target molecules. Although TERS provides diffraction-unlimited spatial resolution similar to that from atomic force microscope, it is time-consuming for large area imaging. Li et al. developed shell-isolated nanoparticle-enhanced Raman spectroscopy (SHINERS), in which SERS-active nanoparticles are coated over the surface with target molecules via wet processes. Lee et al. demonstrated using gold nanorod-loaded filter paper for SERS measurement by pre-wetting and swabbing it on the surface to be probed.

SERS analyses have been performed to analyze biological samples. For example, urine is an easily-accessible bodily fluid that provides metabolic information, including the renal status. Creatinine, a protein metabolite, is one of the major components of human urine besides urea. Since the content of creatinine excreted into the urine is relatively constant in the absence of renal disease, it is used as an internal standard to normalize variations in other urine analytes. Moreover, the detection of creatinine concentration in the urine is important for renal clearance tests, which monitor the filtration function of the kidney. Serum creatinine concentrations are routinely monitored as an indicator of clinical renal function. In clinical diagnostics, serum and urine creatinine concentrations are measured, and generally a high creatinine level indicates kidney problems. For example, normal levels of blood creatinine are approximately 0.6 to 1.2 mg/dl in adult males and 0.5 to 1.1 mg/dl in adult females. In urine, however, creatinine is found to be 500-2000 mg over a 24-hour period. By simply dividing 500-2000 mg to the average urine volume of 1-2 L in an adult male, the lower limit of urine creatinine concentration is estimated to be ~25 mg/dL.

Due to the importance of creatinine in clinical research, a variety of analytical methods have been developed for detecting creatinine in urine, including Jaffe reaction spectrophotometric method, enzymatic method, capillary zone electrophoresis, high performance liquid chromatography (HPLC), high performance thin-layer chromatography (HPTLC), liquid chromatography tandem mass spectrometry (LC-MS), gas chromatography mass spectrometry (GC-MS), isotope dilution extractive electrospray ionization tandem mass spectrometry (ESI-MS), Raman spectroscopy and surface-enhanced Raman scattering (SERS). Compared to traditional analytical methods, Raman and SERS methods offer several advantages. They require no reagents or separation, are non-invasive, are capable of qualitative and quantitative measurements, and provide molecular structure information. In particular, SERS is a highly-sensitive Raman spectroscopic technique where Raman scattering is enhanced primarily by near-field electromagnetic enhancement due to localized surface plasmon resonance (LSPR). Recent advances in the field of nanotechnology have paved the way for the development of SERS based detection.

Most creatinine SERS analyses have thus far been performed on metallic (e.g., Ag and Au) colloidal nanoparticles. In general, Au-based SERS substrates are more stable, nontoxic and biocompatible compared to Ag-based ones, although they have inherently lower (i.e. $10^2$-$10^3$ fold) SERS effects than Ag-based substrates. By using gold colloids, the potential of SERS for qualitative and quantitative creatinine measurements was illustrated by W. R. Premasiri et al., and the measurement of creatinine in human urine at concentrations ranging from 2.56 to 115.2 mg/dl was reported by T. L. Wang et al. Y. Wang et al. performed the detection of creatinine water solution with concentrations ranging from 10-280 mg/dl by mixing with silver colloids. R. Stosch et al. described the determination of creatinine in human serum at physiologically relevant levels using silver colloids as SERS substrates. In addition, nanostructured metal surfaces have been employed for SERS measurements. Compared to metallic colloids, a significant advantage of nanostructure based approach is that SERS signals are more stable against sample ionic strength. This is because the ionic strength can affect the aggregation of metallic colloids and adversely influence reproducibility. H. Wang et al. conducted quantitative analysis of creatinine in the urine of healthy and diabetic patients using Ag-coated parylene nanostructures as the SERS substrate, and successfully detected as low as 6.1 mg/dl urine creatinine. K. W. Kho et al. analyzed urine samples in a microfluidic device embedded with Au-coated polystyrene nanosphere arrays as the SERS substrate. Among existing reports, the lowest detectable concentration was 0.1 µg/ml (~0.88 µM) in water, and 2.56 mg/dl in real urine samples.

Although SERS has the potential for creatinine sensing, both the limit of detection and reproducibility need further improvement for practical application. As mentioned previously, colloidal SERS substrates suffer from sample ionic strength dependent aggregation. Planar nanostructures, on the other hand, may not provide low enough detection limit, because the surface area within the source laser footprint is small and the light-matter interaction is limited. This calls for the development of robust, uniform, and reproducible SERS substrates and reliable measurement techniques.

SUMMARY

The present disclosure relates to label-free, multiplexed, molecular sensing and large-area, high-resolution molecular imaging on a flexible, non-plasmonic surface without solution-phase molecule transfer by stamping surface-enhanced Raman spectroscopy. This disclosure represents a dry physical approach with decent sensitivity and imaging uniformity.

The present disclosure also relates to a novel reagent- and separation-free method for measurement and analysis of target molecules using stamping surface enhanced Raman scattering (S-SERS) technique with nanoporous gold disk (NPGD) plasmonic substrates, a further example of a label-free, multiplexed molecular sensing and imaging technique. The target molecules can be present in the environment or deposited on a substrate for measurement. In preferred examples, the present methods involve the measurement and analysis of biolotical target molecules, such as creatinine present in urine samples.

To produce volumetric SERS effects, nanoporous gold disks (NPGDs) have been developed with large specific areas for effective photothermal conversion and high-density plasmonic hot spots with an average SERS enhancement factor (EF) exceeding $10^8$, which provides a promising platform to meet the needs. NPGDs are hierarchical with the external disk shape and the internal three-dimensional (3D) porous network. NPGDs feature large specific surface area, high-density plasmonic hot-spots, and tunable plasmonics. High-performance SERS substrates have been demonstrated, providing efficient photothermal conversion and light-gated molecular delivery and biomolecular detection in microfluidics. The technique referred to as stamping SERS (S-SERS) for label-free, multiplexed molecular sensing, and large-area, high-resolution molecular imaging provides several benefits such as reagent- and separation-free, low cost, high sensitivity and reproducibility.

In certain applications, a substrate, such as a PDMS thin film, is utilized as a carrier of target molecules. PDMS thin film is preferable for its low cost, ease of fabrication, mechanical flexibility, biocompatibility, relatively few Raman peaks in the fingerprint region, and low auto-fluorescence, although any suitable substrate may be used. Target molecules are first deposited on the substrate, dried, and then stamped onto a NPGD SERS substrate, followed by SERS measurement from "sandwiched" molecules.

In preferred embodiments, a polydimethylsiloxane (PDMS) thin film and nanoporous gold disk SERS substrate play the roles of molecule carrier and Raman signal enhancer, respectively. After stamping the SERS substrate onto the PDMS film, SERS measurements can be directly taken from the "sandwiched" target molecules. The performance of S-SERS has been evaluated by the detection of Rhodamine 6G (R6G), urea, and its mixture with acetaminophen (APAP), in physiologically relevant concentration range, along with corresponding SERS spectroscopic maps. S-SERS features simple sample preparation, low cost, and high reproducibility, which could lead to SERS-based sensing and imaging for point-of-care and forensics applications.

S-SERS has herein been utilized to measure creatinine concentrations in samples of different levels of complexity. The sensing reproducibility of this method using creatinine dissolved in water has been examined. The detection limit, robustness and multiplexing capability using pure creatinine in water, mixtures of creatinine and urea in water, and artificial urine spiked with creatinine have also been examined. Further, creatinine concentration measurements in urines samples collected from a mouse model of nephritis have been performed.

S-SERS is also useful in scenarios in which the target molecules are present in the environment and are not deposited by the user onto a carrier substrate. For example, S-SERS can be used in the forensic analysis of crime scenes or in any exploration in which molecular analysis would be useful. In these applications, the NPGD substrate is stamped directly onto the surface containing the target molecules and then analyzed.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1(a)-(h) shows schematics and corresponding images of S-SERS and NPGDs, including: (a)-(c) sample preparation; (d)-(f) visual images of sample preparation procedures from (a)-(c); (g) SEM image of NPGDs; and (h) SERS along the laser line from 100 µM R6G with average spectrum (black solid line) and ±1 standard deviation (gray shade).

FIGS. 2(a) and (b) shows before ("Normal") and after stamping ("Stamped") SERS for: (a) R6G, and (b) Urea. Insets show (a) variations of R6G peak intensity at 1366 $cm^{-1}$; and (b) variations of Urea peak intensity at 1001 $cm^{-1}$ vs. concentrations.

FIG. 3(a)-(f) shows SERS image of dried 100 µM R6G (top) and 100 µM urea and 1 mM APAP mixture (bottom): (a) bright filed image; (b) SERS map of peak intensity at 1366 $cm^{-1}$ for R6G; (c) spectra obtained at five different positions shown in (b), with the 1366 $cm^{-1}$ peak marked by (*); (d) SERS map of peak intensity at 1001 $cm^{-1}$ for urea; (e) SERS map of peak intensity at 856 $cm^{-1}$ for APAP; and (f) spectra obtained at five different positions shown in (d) and (e), with major peaks for urea (*) and APAP (^) marked.

FIG. 6 (a)-(d) shows S-SERS configuration and NPGD substrate in an example of the current method: (a) photograph of the sandwich sample preparation scheme used in the experiment for creatinine detection; (b) Schematic of NPGD based SERS substrate; and (c)-(d) SEM images of NPGD arrays at the magnification of (c) 100,000× and (d) 250,000×, with the scale bars in SEM images representing 200 nm.

FIG. 7 (a)-(b) shows data indicating reproducibility of S-SERS for creatinine analysis: (a) SERS spectra of 100 μM creatinine detected by S-SERS at ten different locations; and (b) relative intensity variations of major peaks for the ten locations.

FIG. 9 (a)-(c) shows SERS spectra from creatinine and urea water mixture: (a) Concentration-dependent SERS spectra of 100 μM creatinine and 100 mM urea mixed at different volume ratios; (b) a zoomed-in view of the dashed window in (a), showing the intensity variation of creatinine; and (c) a spectra of urea in water.

FIG. 11 (a)-(b) shows the performance of S-SERS on urine from diseased mouse models: (a) concentration-dependent SERS spectra of creatinine in urine samples collected from a nephritic mouse model of anti-GBM disease; and (b) the variations of creatinine peak intensity at 836 $cm^{-1}$ versus creatinine concentration, exhibiting good linearity.

DETAILED DESCRIPTION

The present disclosure relates to the use of a stamping surface enhanced Raman scattering (S-SERS) technique with nanoporous gold disk (NPGD) plasmonic substrates to produce a label-free, multiplexed molecular sensing and imaging technique. The technique is a dry physical approach with decent sensitivity and imaging uniformity. The technique utilizes nanoporous gold disks (NPGDs) with large specific areas for effective photothermal conversion and high-density plasmonic hot spots with an average SERS enhancement factor (EF) exceeding $10^8$. A NPGD SERS substrate is stamped onto a surface containing one or more target molecules for analysis, followed by SERS measurement from "sandwiched" molecules. Alternatively, target molecules are first deposited on a carrier substrate, which can be a PDMS film, optionally dried, and then stamped onto a NPGD SERS substrate for analysis. In preferred embodiments, S-SERS is utilized to measure the concentration of molecules such as glucose and creatinine.

NPG disk arrays can be fabricated directly on a thin PDMS film. Using this as the SERS substrate, in principle any surface can be stamped.

In preferred embodiments, the present technique takes advantage of a substrate, such as PDMS, as a carrier substrate for target molecules and NPGD with high-density hot spots as the Raman signal enhancer, enabling SERS measurement of sandwiched target molecules without solution-phase sample transfer onto the SERS-active surface. R6G and urea detection with concentrations ranging from 10 nM to 100 μM has been demonstrated. Moreover, large-area, high-resolution SERS maps of multiple molecules dried on the PDMS surface has been demonstrated. By coupling with high-throughput Raman imaging systems based on line-scan or active-illumination, this technique can become a powerful tool for forensics analysis. The capabilities of detecting and imaging physiological concentrations of biological samples could lead to new point-of-care applications.

The present technique also includes a reagent- and separation-free method to determine creatinine concentrations in urine based on stamping SERS and nanoporous gold disk SERS substrates. The reproducibility has been demonstrated by detecting 100 μM creatinine with relative intensity variations ranging from −12% to 12% across multiple samplings. The detection of creatinine water solutions in the 100 nM to 100 μM range has been demonstrated with good linearity, representing the first demonstration of sub-μM creatinine sensing by any reagent- and separation-free technique. Moreover, excellent concentration-dependent creatinine sensing was successfully demonstrated in samples of increasing complexity: urea water mixture, artificial urine, and urine from nephritic mice. In particular, an unprecedented detection limit of ~0.68 mg/dl has been achieved in urine samples from nephritic mice. This is a significant milestone because it approaches the performance of commercial creatinine kits, however, without the need for reagent and time-consuming assays. This method will provide a viable alternative for urine creatinine quantification without the need for reagents or separation. Such technology would provide invaluable information and utility in renal function monitoring and disease diagnosis at both hospitals and point-of-care scenarios.

Generally, preferred embodiments of the present method of molecular sensing and imaging using stamping surface-enhanced Raman spectroscopy (S-SERS) involve depositing a surface-enhanced Raman spectroscopy (SERS) substrate on top of at least one target molecule contained on a surface, stamping the SERS substrate onto the surface to produce a stamped SERS surface, and taking SERS measurements directly from the target molecule, wherein the target molecule is positioned between the stamped SERS substrate and the surface, and wherein the SERS measurements provide sensing and imaging information about the target molecule. In additional preferred embodiments, the target molecule is first deposited on the surface, and the surface is a carrier substrate.

Other preferred embodiments include an apparatus for molecular sensing and imaging using stamping surface-enhanced Raman spectroscopy (S-SERS) which comprises a surface-enhanced Raman spectroscopy (SERS) substrate stamped onto a surface containing a target molecule, and a device for taking SERS measurements directly from the target molecule, wherein the SERS measurements provide sensing and imaging information about the target molecule. The target molecule may be present on the surface or may be deposited on the surface.

In preferred embodiments, a carrier substrate is used for depositing the target molecules. The carrier substrate may be polydimethylsiloxane (PDMS) film and the SERS substrate comprises a nanoporous gold disk (NPGD). The target molecule may also be dried after it is deposited on the carrier substrate. The device used for taking SERS measurements directly from the target molecule may be a Raman microscopy system. Examples of target molecules include Rhodamine 6G (R6G), urea, acetaminophen (APAP), glucose, creatinine, or a combination thereof. In certain embodiments, the target molecule is contained in a sample. The sample may be a biological sample collected from a subject, such as urine. The sensing and imaging information collected using the method may be information confirming the presence of the target molecule, or information regarding the concentration of the target molecule.

EXAMPLE 1

S-SERS Scheme

Figure 1:
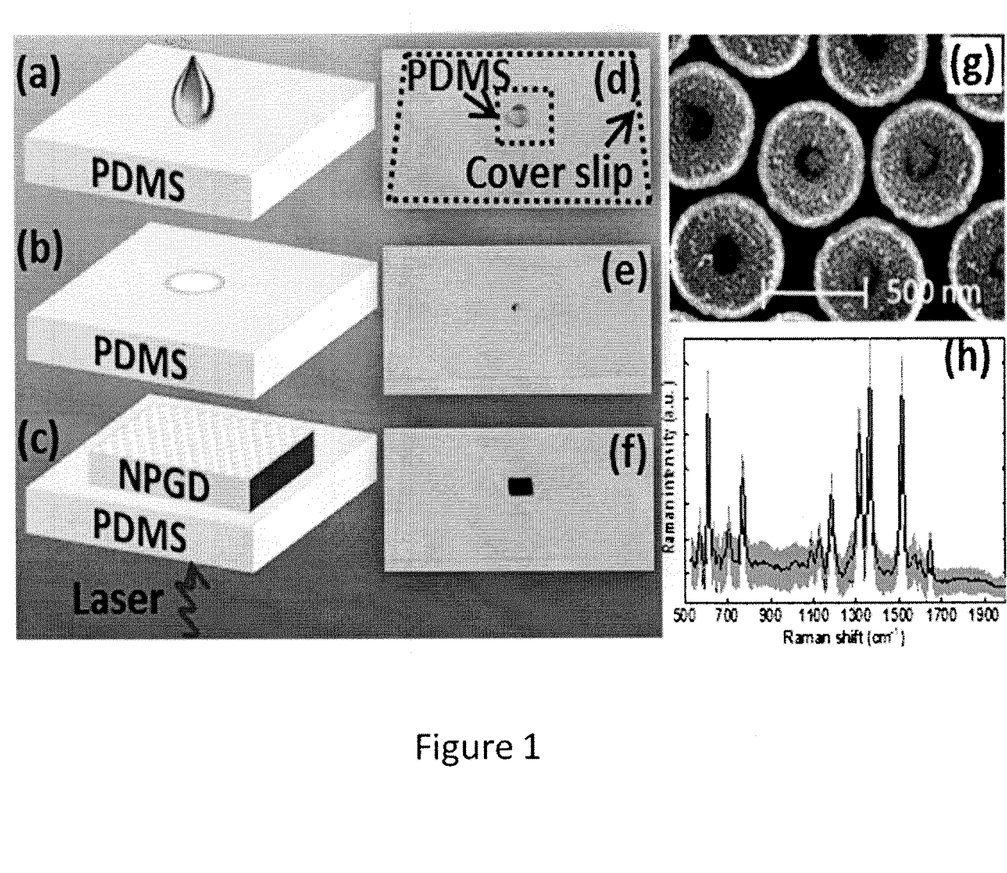

FIG. 1(a-c) illustrate an example of the S-SERS scheme with corresponding visual images shown in FIG. 1(d-f). First, 4 µL of the prepared solution containing target molecules was dropped on the PDMS (Sylgard 184, Dow Corning) thin film having a thickness of ~125 µm and a dimension of ~1×1 $cm^2$ (see FIGS. 1(a) and 1(d)), which was prepared following standard protocols. The droplet was then dried on the PDMS substrate, forming an ultra-thin film of target molecules on the PDMS surface after solvent evaporation in around 30 min (see FIGS. 1(b) and 1(e)). Finally, a NPGD substrate was stamped onto the PDMS surface with dried molecules, followed by focusing laser at the PDMS surface to detect SERS signals of sandwiched molecules (see FIGS. 1(c) and 1(f)). Monolayer NPGDs densely distributed on Au-coated silicon substrates were fabricated by the nanosphere lithography (NSL) technique as previously described (M. Li, J. Lu, J. Qi, F. Zhao, J. Zeng, J. C.-C. Yu, and W.-C. Shih, "Stamping surface-enhanced Raman spectroscopy for label-free, multiplexed, molecular sensing and imaging," Journal of Biomedical Optics 19(5), 050501 (2014), incorporated by reference herein). A scanning electron microscopy (SEM) image was acquired to show the structure of the NPGDs (see FIG. 1(g)) before stamping.

A home-built line-scan Raman microscopy system with 785-nm excitation laser was employed. The laser power on the sample was ~28 mW over a 1×133 $µm^2$ line-shaped area, and all the samples were measured with an integration time of 10-20 sec for each scan step. To verify the performance of the proposed technique, R6G with well-characterized SERS spectrum was used. A 4 µL droplet of 100 µM R6G was dropped and dried on the PDMS surface, resulting in a ~1 mm spot. First, the measurement uniformity was examined by imaging a region around the mid-point between the center and circumference of the dried spot, which appeared visually uniform under bright-field microscopy. FIG. 1(h) shows the statistics of a total of 350 SERS spectra across the laser line where the solid line representing average spectrum while the gray shade representing ±1 standard deviation. The results suggest decent SERS uniformity across the sampled region.

Figure 2:
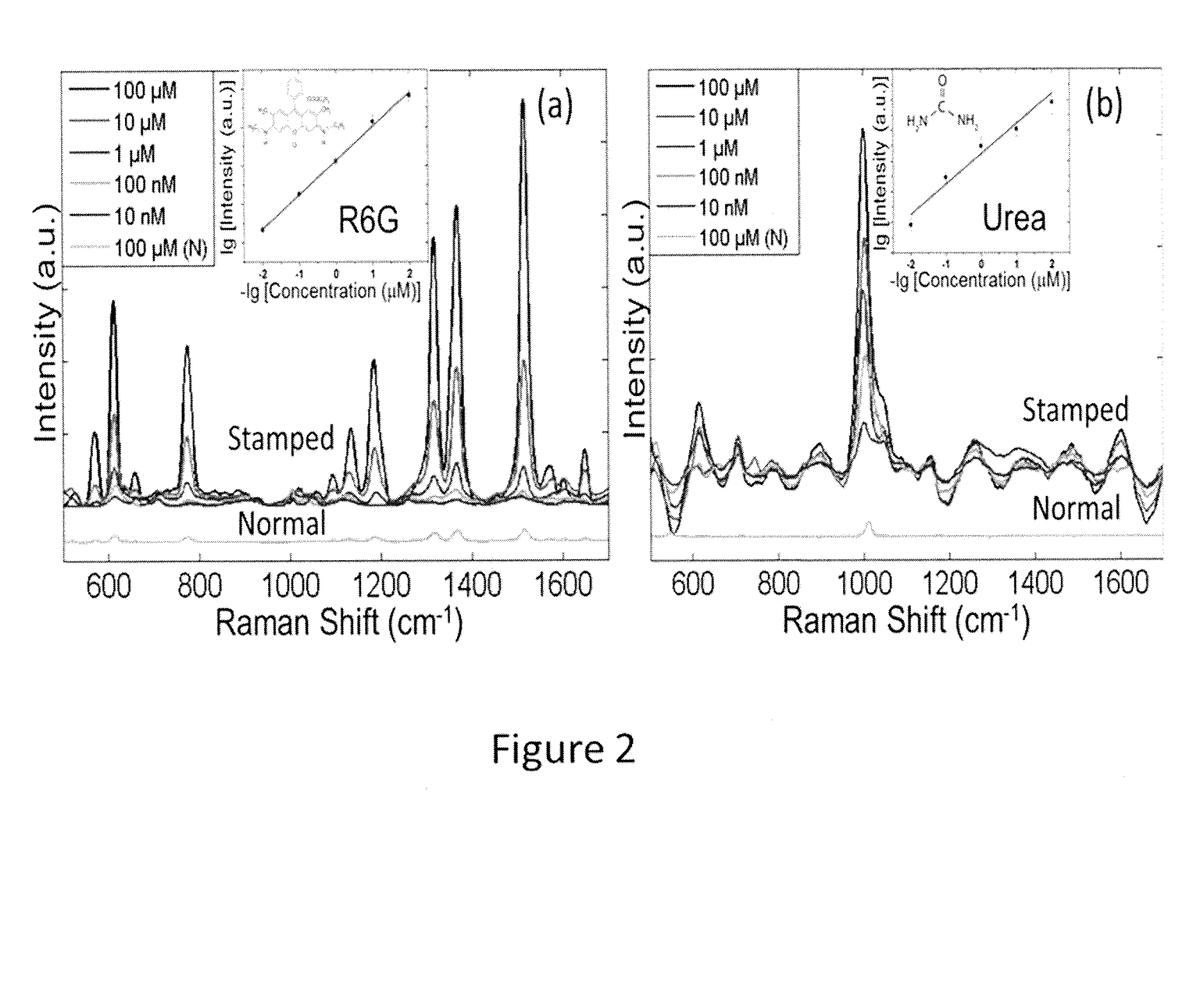

Next, it is shown that S-SERS can reveal apparently invisible molecular coatings on PDMS. As shown in FIG. 2(a), R6G Raman spectrum from dried 100 µM solutions on PDMS surface was measured and marked as "Normal". No normal Raman spectrum was observed from any samples with lower concentrations. NPGD substrate was then gently stamped against the PDMS, after which the sample was measured again and marked as "Stamped". Major Raman peaks for R6G at 611, 771, 1185, 1317, 1366, 1515 and 1650 $cm^{-1}$ were observed. The 1366 $cm^{-1}$ peak intensity for 100 µM R6G exhibits a ~10-fold enhancement after stamping.

EXAMPLE 2

S-SERS Applications

To examine the capability of the stamping protocol for potential point-of-care and forensics applications, urea solutions with different concentrations ranging from 10 nM to 100 µM were used to simulate urine tests. The same sample preparation and measurement procedures aforementioned were applied. As shown in FIG. 2(b), excellent intensity enhancement can be seen after stamping, with the primary Raman peak near 1001 $cm^{-1}$ corresponding to the symmetrical C-N stretching vibration mode clearly observed. The detection limit in the nanoMolar range is significantly lower than most SERS results reported in the literature in the milliMolar range, although direct comparison is not suggested because the present technique employed dried samples as opposed to continuous-flow measurements in microfluidic configurations.

Conventional SERS measurements by transferring molecules of interest to SERS-active substrates can result in the unavoidable loss of spatial distribution of molecules on the original surface. To further demonstrate that the S-SERS technique has the capability to obtain spatio-chemical information from the PDMS surface, a 3-dimensional (x, y, λ) SERS map was recorded from dried 100 µM R6G samples. The SERS map generated by peak intensity at 1366 $cm^{-1}$ (FIG. 3(b)) showed an identical yet clearer boundary of dried R6G droplet compared with the bright-field image (FIG. 3(a)). Five different points inside the droplet were chosen, and the corresponding spectra were shown in FIG. 3(c).

Figure 3:
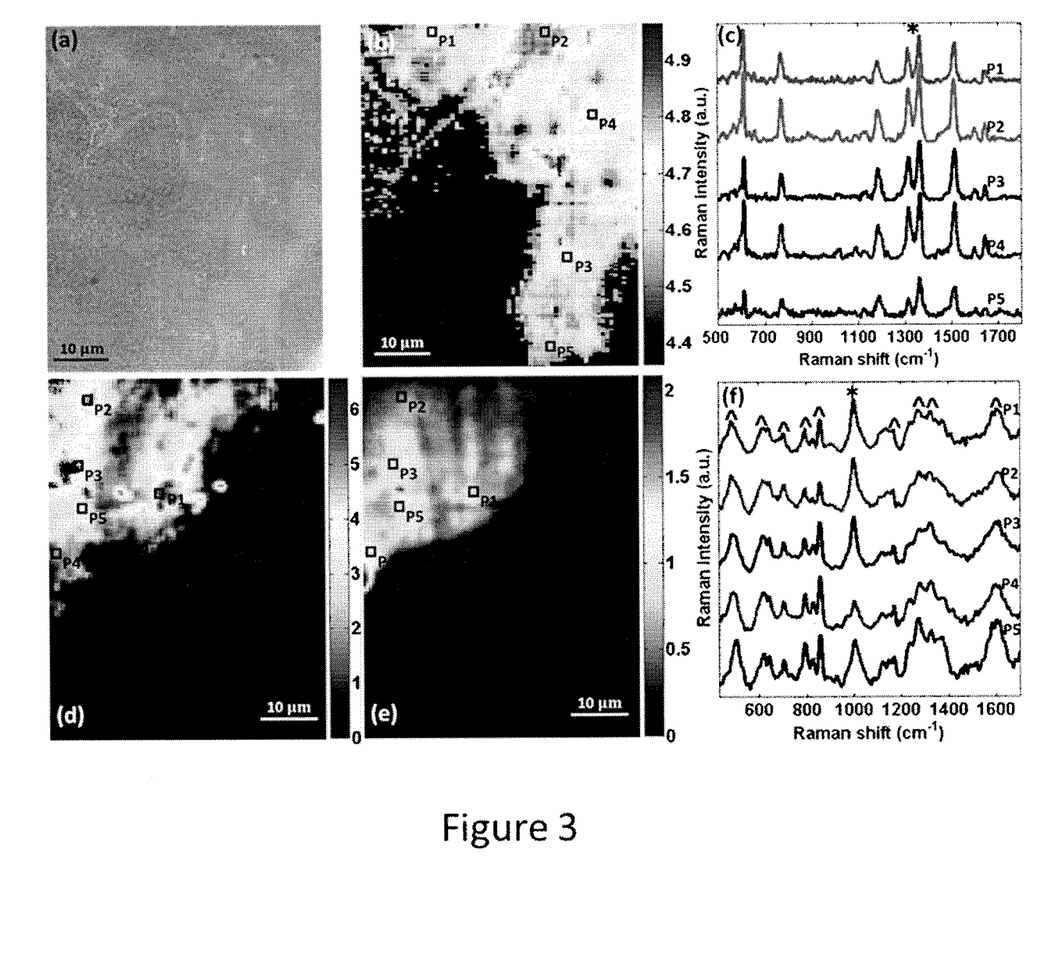

To demonstrate multiplexed sensing and imaging capabilities, a 3-dimensional (x, y, λ) SERS map was recorded from dried mixture samples of 100 µM urea and 1 mM acetaminophen (APAP). These concentrations are relevant for successful detection in urine. After stamping, the dry mark could not be found using bright-field microscopy because both molecules are colorless; however, SERS maps successfully provided the spatial distribution information of both. As shown in the bottom row of FIG. 3, the SERS map generated by peak intensity at 1001 $cm^{-1}$ for urea (FIG. 3(d)) showed a similar overall boundary of dried droplet to the one generated by peak intensity at 856 $cm^{-1}$ for APAP (FIG. 3(e)), but different spatial distribution. As shown in FIG. 3(f), spectra from five different positions were presented. For example, the peak intensity ratio of urea's major peak at 1001 $cm^{-1}$ to that of APAP at 856 $cm^{-1}$ is 2.45 at position 2 (P2), while the ratio is 0.67 at position 4 (P4). The results suggest that the two different molecules did not uniformly distribute on the PDMS surface during drying, likely due to differences in density, solubility, concentration, and affinity to the PDMS surface, etc. The mixture data were collected from the circumference to emphasize the detection of the drying edge, where the well-known "coffee ring" effect caused more molecular accumulation.

Figure 4:
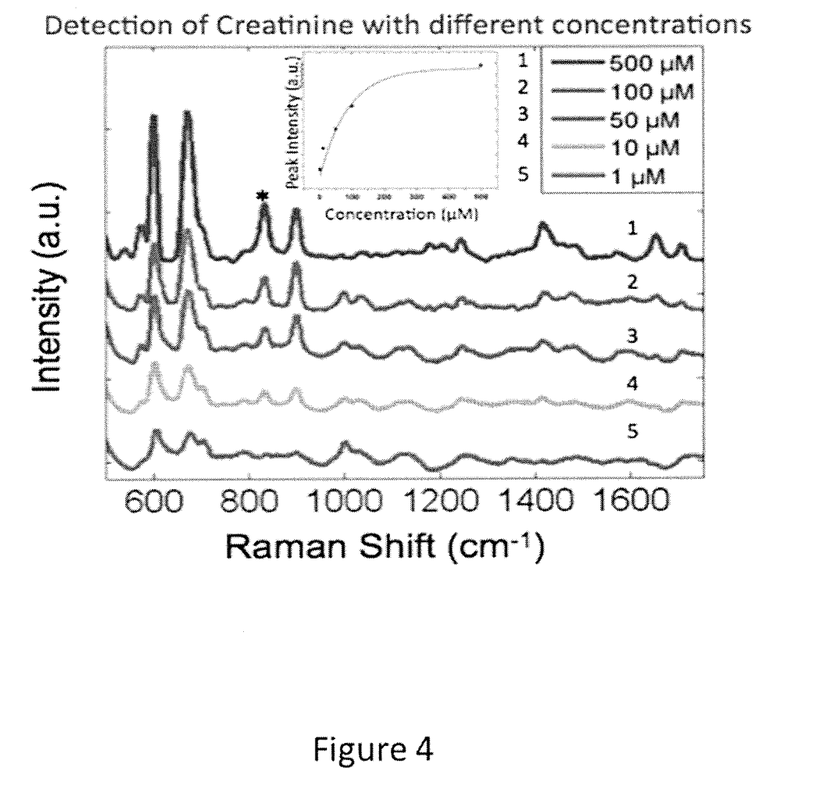
FIG. 4 shows SERS spectra obtained at varying concentrations of creatinine.
Figure 5:
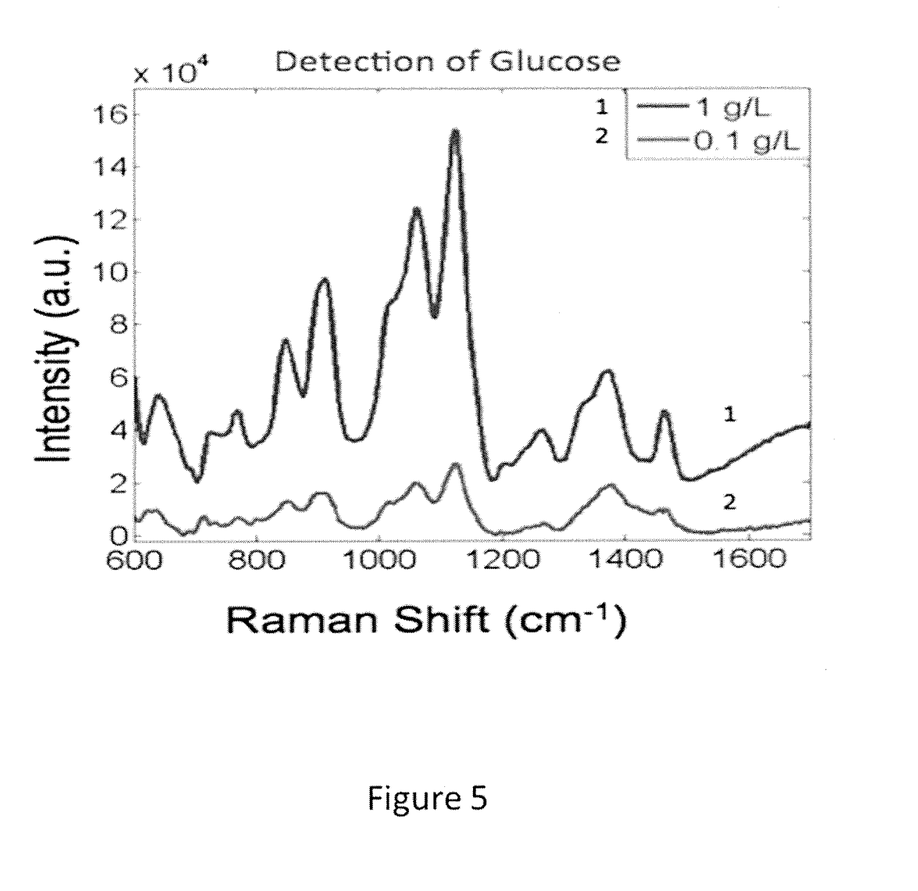
FIG. 5 shows SERS spectra obtained at varying concentrations of glucose.

Physiologically important analytes such as glucose and creatinine can be measured by the Stamp-SERS protocol at physiologically relevant concentrations. See FIGS. 4 and 5 for the SERS spectra obtained for different concentrations of creatinine and glucose.

EXAMPLE 3

Detection of Creatinine

Creatinine (C4255, anhydrous, ≥98%) and urea (U5378, powder) were purchased from Sigma-Aldrich. Sample solutions of individual molecules were prepared by dissolving the powders in deionized (DI) water, and then diluted to various concentrations. Sodium chloride, potassium, and sodium phosphate (monobasic, monohydrate) were purchased from Macron™ Chemicals. Artificial urine was prepared using 24.2 g urea, 10 g sodium chloride, 6.0 g potassium, and 6.4 g sodium phosphate (monobasic, monohydrate) dissolved in 1 L DI water. Polydimethylsiloxane (PDMS, Sylgard 184, Dow Corning) was prepared by thoroughly mixing base and curing agent at a weight ratio of 10:1, and then poured over the bottom surface of a petri dish, degassed, and finally cured on a hot plate at 70° C. for 1 h.

In these experiments, large-area, uniform, and reproducible NPGD arrays patterned on Au-coated silicon substrate were utilized as SERS substrates. NPGDs were fabricated with Ag—Au alloy ($Ag_{70}Au_{30}$, atomic ratio 70:30) using a process similar to nanosphere lithography (NSL). The detailed procedure has been previously reported (M. Li, J. Lu, J. Qi, F. Zhao, J. Zeng, J. C.-C. Yu, and W.-C. Shih, "Stamping surface-enhanced Raman spectroscopy for label-free, multiplexed, molecular sensing and imaging," Journal of Biomedical Optics 19(5), 050501 (2014), incorporated by reference herein). Briefly, the fabrication process started with depositing layers (20 nm Cr/200 nm Au) by evaporation on a clean silicon wafer, and then a 120 nm-thick Ag/Au alloy layer by sputtering. After that, a monolayer of 460 nm-diameter polystyrene (PS) beads serving as masks was deposited onto the surface. A two-step plasma treatment was performed subsequently: oxygen and argon treatment to shrink PS beads and etch away the unprotected portion of the alloy film, respectively. Finally, NPGDs were formed by removing PS residues by sonication in chloroform, and dealloying in concentrated nitric acid.

SERS measurements were performed using a home-built line-scan system with a 785-nm continuous-wave (CW) Titanium:Sapphire laser (3900S, Spectra-Physics). The excitation laser was shaped into a 1×133 $\mu m^2$ line at the sample plane. The SERS spectra were recorded by a spectrograph-charge coupled device (CCD) system (LS-785, PlActon) controlled by Winspec software (PlActon), and post-processed using Matlab (Mathworks). Spectroscopic backgrounds were approximated by a $5^{th}$ order polynomial and removed. Image curvature due to off-axis light incidence and the large-area CCD detector was corrected by a software technique.

Figure 6:
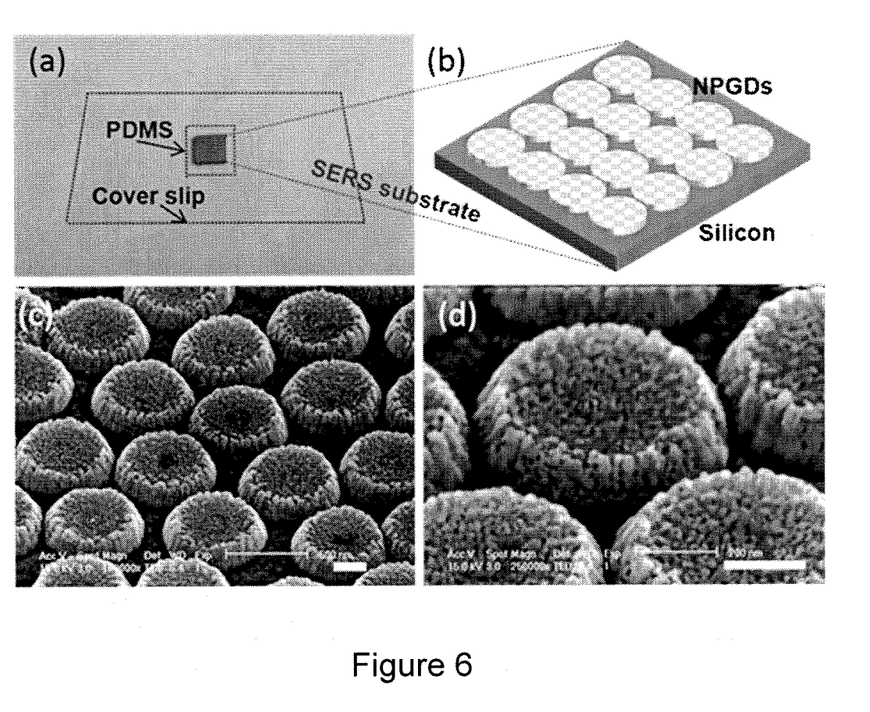

FIG. 6(a) shows the sample configuration used in the experiment. First, a 1 µL droplet of the prepared solution containing the target molecules (i.e. creatinine) was first pipetted onto a PDMS thin film (~1×1 $cm^2$, ~100 µm thick) laid flat on a glass coverslip. The droplet was then dried on the PDMS substrate, forming a film of target molecules after solvent evaporation. After that, a NPGD substrate (~0.5×0.5 $cm^2$) was stamped onto the PDMS surface bearing dried target molecules. Finally, the laser was focused at the PDMS surface to detect SERS signals from the sandwiched target molecules. Compared to directly drying the droplet onto the NPGD substrate, where target molecules are permanently chemically bound to the SERS substrate, the related issues like competitive adsorption among different molecules, surface and molecule affinity variability and uncertainty are reduced to some extent by the S-SERS technique. FIG. 6(b) shows the schematic of the NPGD arrays serving as Raman signal enhancers. Scanning electron microscope (SEM) images recorded are shown in FIGS. 6(c) and 6(d) to illustrate the structure and morphology of the NPGD arrays. The fabricated NPGDs have average diameter, thickness, and pore size of ~300, 75, and 14 nm, respectively.

Figure 7:
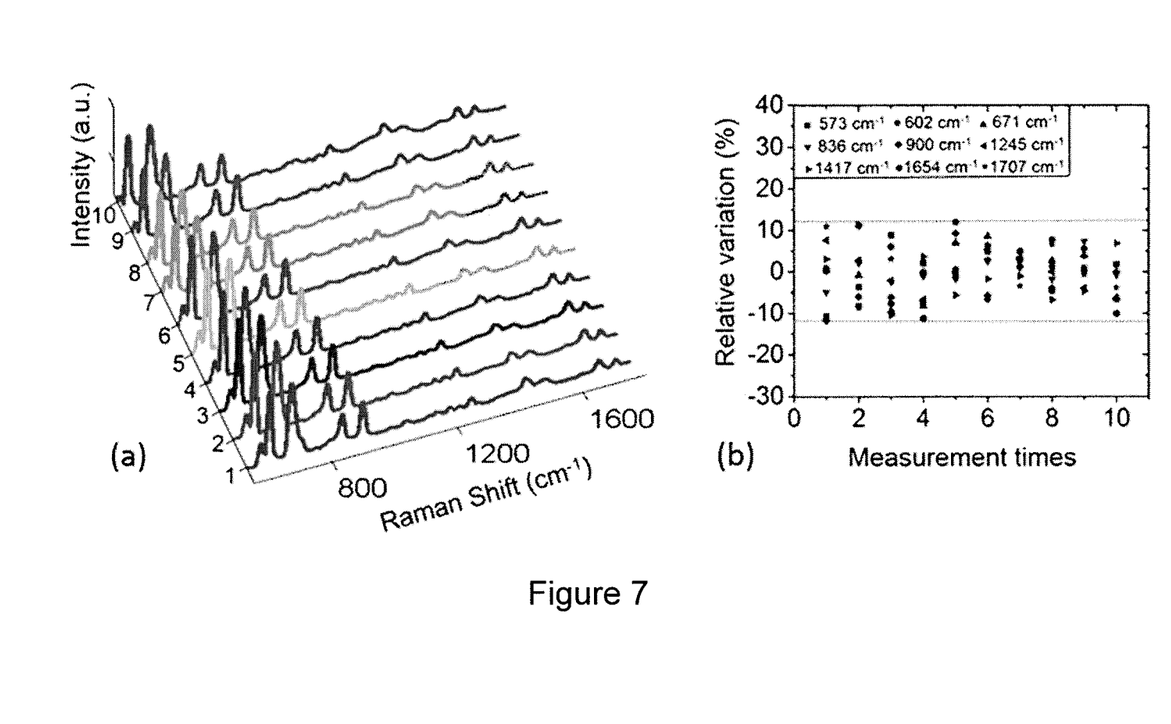

To demonstrate reproducibility of S-SERS for creatinine analysis, a 1 µL droplet of 100 µM creatinine was pipetted and dried on the PDMS surface, resulting in a spot with a diameter of ~0.5 mm. NPGD substrate was then gently stamped against the PDMS film with creatinine until intimate contact was formed, after which the sample was measured from the coverslip side. SERS spectra were acquired with 30 mW laser power and 10 sec acquisition time each. The laser power density was estimated to be 0.25 mW per $\mu m^2$. FIG. 7 shows highly-reproducible SERS spectra from ten randomly chosen locations 100 µm away from the circumference of the drying mark of creatinine droplet, where dominant SERS peaks corresponding to creatinine, i.e. 573, 602, 671, 836, 900, 1245, 1417, 1645, and 1707 $cm^{-1}$ were identified. As shown in FIG. 7(b), the relative intensity variations of the major creatinine peaks were calculated to be within −12% to 12% of the average intensity, when repeatedly assayed from different locations. Similar reproducibility has been obtained from previous NPGD substrates.

Figure 8:
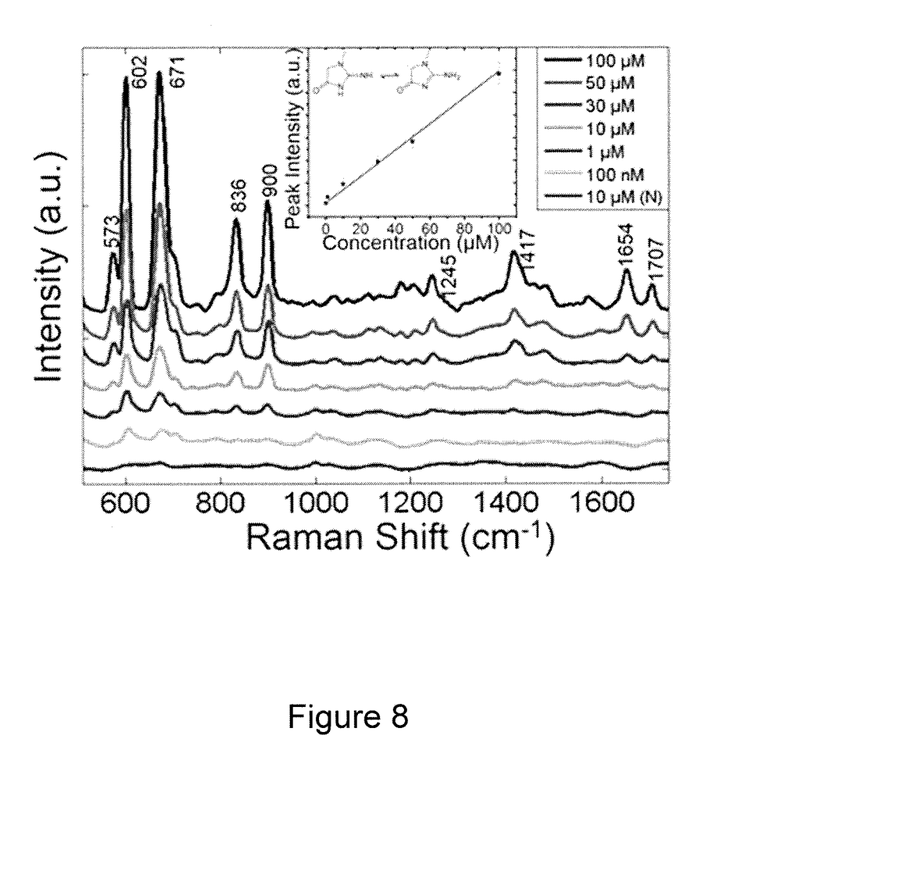
FIG. 8 shows concentration-dependent SERS spectra of creatinine measured by S-SERS at concentration ranging from 100 nM to 100 μM. The insets indicate the variations of creatinine peak intensity at 836 $cm^{-1}$ as a function of creatinine concentration and the molecular structure of creatinine. The error bars represent the standard deviation from five measurements.

In order to further assess the sensing capability of S-SERS for creatinine analysis, measurements were performed for creatinine water solutions of different concentrations ranging from 100 nM to 100 µM. The measurements for each creatinine concentration were performed five times with 30 mW laser power and 20 sec CCD integration time. The resulting averaged SERS spectra are shown in FIG. 8, where major creatinine Raman peaks were identified in all spectra, and the peak intensity increased with increasing creatinine concentration. The Raman spectrum of 10 µM creatinine before stamping is also presented at the bottom for comparison (black line), where creatinine peaks can hardly be identified. In contrast, S-SERS provides excellent creatinine spectrum at concentrations as low as 100 nM. The limit of detection of creatinine in water is estimated to be 13.2 nM based on the signal to noise ratio (22.7) at 100 nM. The inset shows a good linear relationship of intensity variations of the 836 $cm^{-1}$ peak as a function of creatinine concentration within the range of 100 nM to 100 µM.

Figure 9:
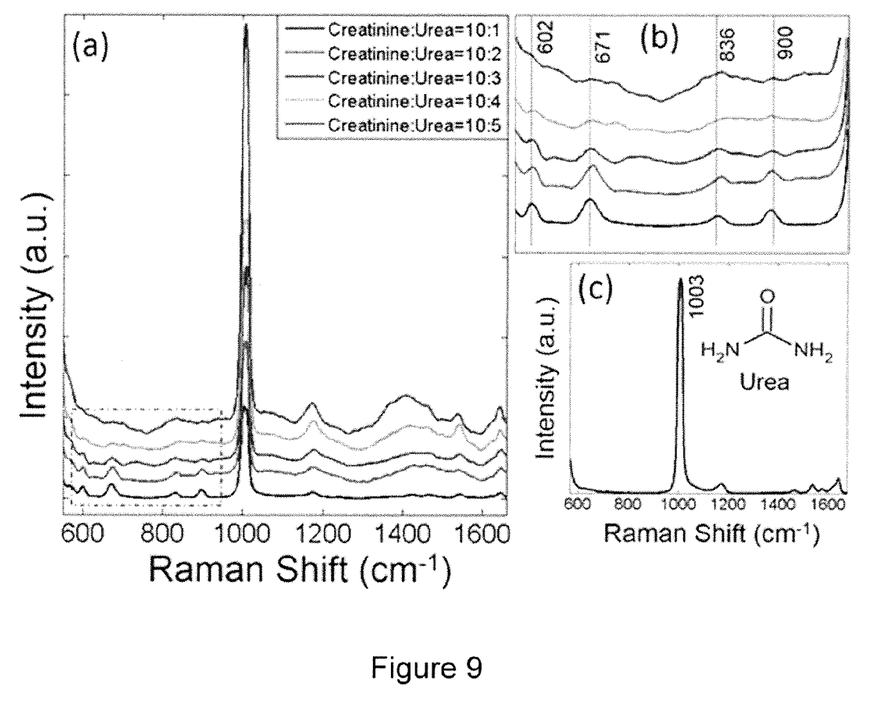

Since urea is a dominant chemical constituent in urine samples, a reagent- and separation-free technique needs to provide selectivity based on intrinsic molecular fingerprints. To demonstrate the multiplexed sensing capabilities of S-SERS, measurements were performed on samples prepared by mixing 100 µM creatinine and 100 mM urea solutions at five different volume ratios, namely 10:1, 10:2, 10:3, 10:4, and 10:5. The resultant concentration of creatinine ranges from 66.7 to 90.9 µM, and urea ranges from 9 to 33 mM. Both concentration ranges correspond to physiological concentrations in urine, and are relevant for practical urine analysis. Five measurements were conducted for each volume ratio to obtain the averaged spectra and standard deviation. The averaged SERS spectra of creatinine and urea mixture at five different ratios are shown in FIG. 9. Correlation between peak intensity and concentration can be identified for both creatinine (i.e. at 602, 671, 836 and 900 $cm^{-1}$) and urea (i.e. at 1003 $cm^{-1}$). The results show that concentration-dependent creatinine SERS can be obtained even in the co-presence of ~100× higher concentration of urea. In addition, the creatinine peak intensity from pure creatinine and was compared to the mixture of creatinine and urea (i.e., FIG. 8 versus FIG. 9). The intensity at ~836 $cm^{-1}$ from the mixture (FIG. 9) was about 17% lower than that from the pure sample (FIG. 8). This could be attributed to preferential surface crowding: urea, besides being present at higher concentration, may occupy more surface area on the PDMS film than creatinine. In addition, high concentration urea would change the refractive index, thus affecting laser spot size and collection efficiency.

EXAMPLE 4

Detection of Creatinine in Urine

Figure 10:
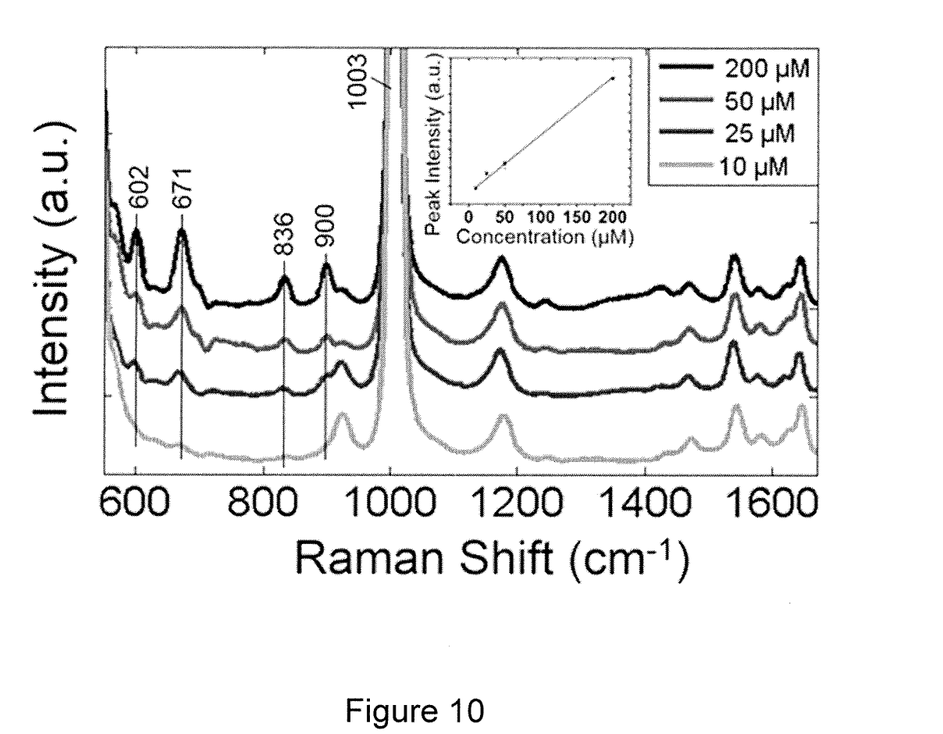
FIG. 10 shows concentration-dependent SERS spectra of creatinine in artificial urine spiked with creatinine at concentrations of 10, 25, 50 and 200 μM. The inset shows creatinine peak intensity at 836 $cm^{-1}$ versus concentration.

In order to test the capability of S-SERS for quantitative analysis of creatinine in a more complex mixture, creatinine was added to artificial urine with resultant concentrations of 10, 25, 50 and 200 μM. Each sample was measured five times, and the averaged SERS spectra are shown in FIG. 10. From spot to spot, the urea signature peak at 1003 cm$^{-1}$ shows an intensity variation of less than 5%, which further indicates the high reproducibility of S-SERS. Moreover, with the increase of creatinine concentration, the major peaks for creatinine (i.e. 602, 671, 836 and 900 cm$^{-1}$) increased in intensity. The inset indicates the variations of creatinine peak intensity at 836 cm$^{-1}$ as a function of creatinine concentration, and a good linearly relationship is observed. The creatinine peak intensity at the same concentration (i.e. 10 μM) from pure creatinine was also compared to creatinine in artificial urine (i.e., FIG. 8 versus FIG. 10). The intensity at ~836 cm$^{-1}$ from the doped artificial urine sample (FIG. 10) was about 35% lower than that from the pure creatinine sample (FIG. 8). This is likely primarily due to preferential surface crowding by other molecules in the mixture.

S-SERS was further employed to measure creatinine in urine samples collected from nephritic mice with anti-GBM disease induced as described before. The "ground truth" creatinine concentrations in these samples from different mice were determined using a commercial colorimetric assay kit based on a coupled enzyme reactions (#80350, Crystal Chem, Inc.) with a detection limit ~0.15 mg/dl according to product specifications. In this assay, the creatinine is broken down to creatine, and then converted to sarcosine. The sarcosine is oxidized to hydrogen peroxides, which react with peroxidase, and can be quantified by measuring light absorption at 550 nm. The entire assay from warming up reagents to room temperature to calculating creatinine concentration would take ~1 hour at the very least.

Figure 11:
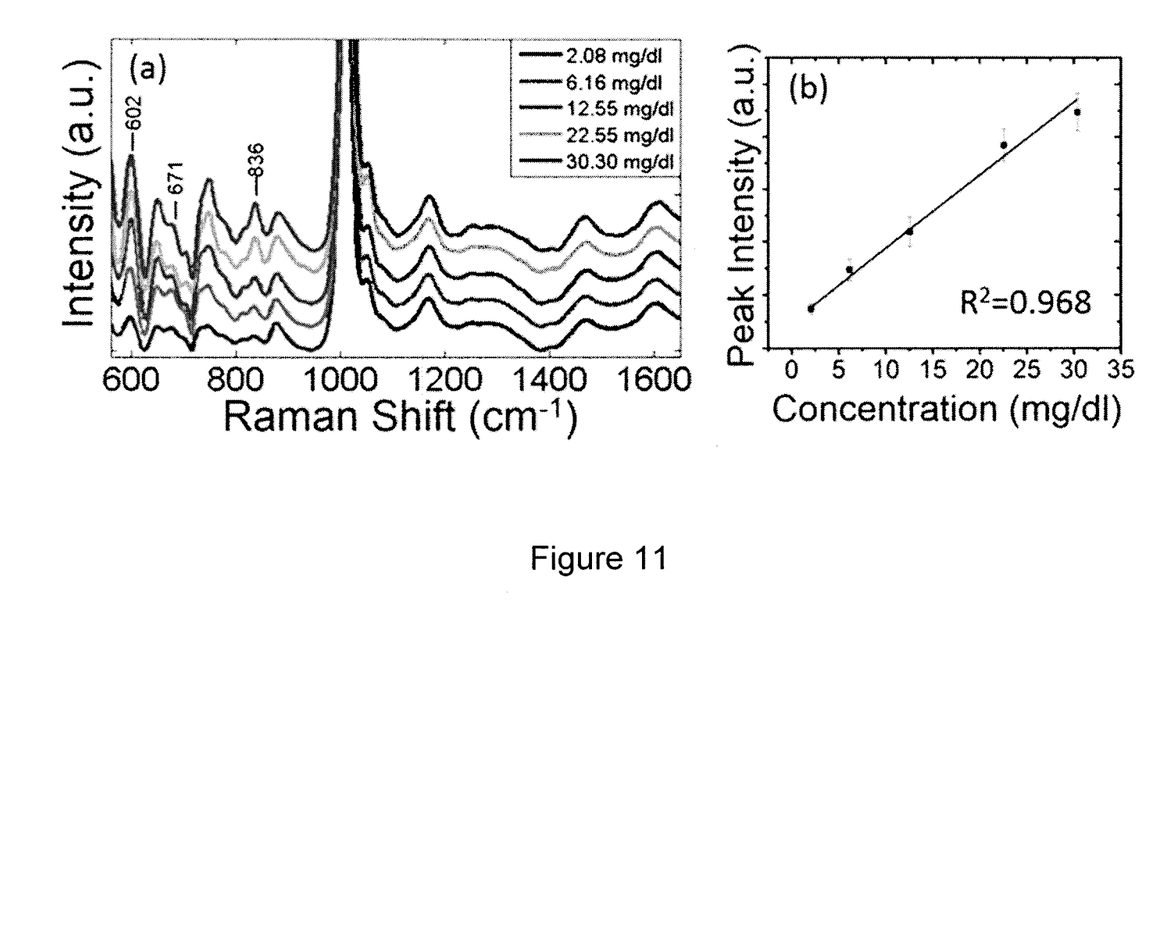

FIG. 11(a) shows averaged SERS spectra of the different mouse urine samples with creatinine concentrations at 2.08, 6.16, 12.55, 22.55, and 30.30 mg/dl. 1 mg/dL corresponds to 88.4 μM for creatinine in water. The major SERS peaks of creatinine at 602, 671, and 836 cm$^{-1}$ can once again be identified in the mouse urine samples. A good linear relationship is observed by plotting the peak intensity at 836 cm$^{-1}$ versus creatinine concentrations as shown in FIG. 11(b). Although the lowest concentration in this experiment was 2.08 mg/dl, the limit of detection is estimated to be 0.68 mg/dl based on the signal to noise ratio (9.14) at 2.08 mg/dl. When one compares the creatinine peak intensity at ~836 cm$^{-1}$ from real urine to that of creatinine water solution at the same concentration (i.e. FIG. 8), the intensity from real urine is about 6-fold lower than that from the creatinine water solution. Besides preferential surface crowding from other urine analytes and proteins, this difference may relate to the non-transparent, dark yellow color of the urine, which might have caused light attenuation and local refractive index changes. The results show that this new approach provides a reagent- and separation-free method for creatinine concentration measurements in real urine samples. It is remarkable that S-SERS is still able to capture the creatinine-specific signature despite the co-existence of >70 proteins in these nephritic urine samples. This is attributed to the intrinsic molecular fingerprinting capability of Raman and SERS spectroscopy.

The invention claimed is:

1. A method of molecular sensing and imaging using stamping surface-enhanced Raman spectroscopy (S-SERS), the method comprising:
    (a) depositing a surface-enhanced Raman spectroscopy (SERS) substrate on top of a surface comprising at least one target molecule;
    (b) stamping the SERS substrate onto the surface to produce a stamped SERS surface; and
    (c) taking SERS measurements directly from the at least one target molecule, wherein the at least one target molecule is positioned between the stamped SERS substrate and the surface, and wherein the SERS measurements provide sensing and imaging information about the target molecule.

2. The method of claim 1, further comprising the step of depositing at least one target molecule on the surface before depositing the surface-enhanced Raman spectroscopy (SERS) substrate, wherein the surface is a carrier substrate.

3. The method of claim 2, wherein the carrier substrate is a polydimethy siloxane (PDMS) film.

4. The method of claim 2, wherein the step of depositing at least one target molecule on the surface further comprises drying the at least one target molecule.

5. The method of claim 2, wherein the target molecule is contained in a sample.

6. The method of claim 5, wherein the sample is a biological sample collected from a subject.

7. The method of claim 1, wherein the SERS substrate comprises a nanoporous gold disk (NPGD).

8. The method of claim 1, wherein the target molecule is Rhodamine 6G (R6G), urea, acetaminophen (APAP), glucose, creatinine, or a combination thereof.

9. The method of claim 1, wherein the sensing and imaging information is information confirming the presence of the target molecule.

10. The method of claim 1, wherein the sensing and imaging information is information regarding the concentration of the target molecule.

11. The method of claim 1, wherein the step of taking SERS measurements directly from the at least one target molecule is performed by a Raman microscopy system.

12. An apparatus for molecular sensing and imaging using stamping surface-enhanced Raman spectroscopy (S-SERS) comprising:
    a surface-enhanced Raman spectroscopy (SERS) substrate stamped onto a surface on top of at least one target molecule; and
    a device for taking SERS measurements directly from the at least one target molecule, wherein the SERS measurements provide sensing and imaging information about the target molecule.

13. The apparatus of claim 12, wherein the surface is a carrier substrate, and wherein the at least one target molecule is deposited on the carrier substrate.

14. The apparatus of claim 13, wherein the carrier substrate is polydimethylsiloxane (PDMS) film.

15. The apparatus of claim 13, wherein the target molecule is contained in a sample.

16. The apparatus of claim 15, wherein the sample is a biological sample collected from a subject.

17. The apparatus of claim 12, wherein the SERS substrate comprises a nanoporous gold disk (NPGD).

18. The apparatus of claim 12, wherein the device for taking SERS measurements is a Raman microscopy system.

19. The apparatus of claim 12, wherein the target molecule is Rhodamine 6G (R6G), urea, acetaminophen (APAP), glucose, creatinine, or a combination thereof.

20. The apparatus of claim 12, wherein the sensing and imaging information is information confirming the presence of the target molecule.

21. The apparatus of claim 12, wherein the sensing and imaging information is information regarding the concentration of the target molecule.

\* \* \* \* \*

UNITED STATES PATENT AND TRADEMARK OFFICE
CERTIFICATE OF CORRECTION

PATENT NO. : 9,546,958 B2  
APPLICATION NO. : 14/699025  
DATED : January 17, 2017  
INVENTOR(S) : Shih Page 1 of 1

It is certified that error appears in the above-identified patent and that said Letters Patent is hereby corrected as shown below:

In the Claims

Column 12, Line 22, Claim 3, delete "polydimethy siloxane" and insert -- polydimethylsiloxane --, therefor.

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*